United States Patent
Agterof et al.

[11] Patent Number: 6,033,717
[45] Date of Patent: Mar. 7, 2000

[54] METHOD FOR PRESERVATION UNDER PRESSURE

[75] Inventors: Wim Agterof; Hubertus L Lelieveld; Thomas Reichelt; Johannes P Smelt, all of Vlaardingen, Netherlands

[73] Assignee: Unilever Patent Holdings, Vlaardingen, Netherlands

[21] Appl. No.: 09/180,746

[22] PCT Filed: May 15, 1997

[86] PCT No.: PCT/EP97/02711

§ 371 Date: Jul. 12, 1999

§ 102(e) Date: Jul. 12, 1999

[87] PCT Pub. No.: WO97/43914

PCT Pub. Date: Nov. 27, 1997

[30] Foreign Application Priority Data

May 17, 1996 [EP] European Pat. Off. .............. 96201388

[51] Int. Cl.[7] .............................. A23L 3/015; A61L 2/02
[52] U.S. Cl. ............................ 426/665; 426/330; 422/33; 422/295; 99/453; 99/467; 99/483
[58] Field of Search .................................. 426/330, 665; 422/10, 33, 295; 99/453, 467, 477, 483

[56] References Cited

U.S. PATENT DOCUMENTS 5,316,745  5/1994  Ting et al. .............................. 422/295
5,840,353  11/1998  Woolner .................................. 426/15

FOREIGN PATENT DOCUMENTS

| 628 253 | 12/1994 | European Pat. Off. . |
| 727 227 | 8/1996 | European Pat. Off. . |
| 2 675 544 | 10/1992 | France . |
| 44 06 028 | 8/1995 | Germany . |
| 95 23637 | 9/1995 | WIPO . |
| 97/21361 | 6/1997 | WIPO . |
| 97/43914 | 11/1997 | WIPO . |

OTHER PUBLICATIONS

Search Report WO/9743814, Sep. 19, 1997.

*Primary Examiner*—Nina Bhat
*Attorney, Agent, or Firm*—Pillsbury Madison & Sutro LLP

[57] ABSTRACT

Method for substantially decreasing the viability of microorganism and deactivating enzymes in a contaminated substance by exerting a high pressure the substance. The substance is conducted in a steady flow through and open narrow tube while the pressure difference between the entrance and the exit of the tube is maintained at 100 Mpa or more. The temperature rise of the product while passing through the tube can be confined to less than 5° C. The method provides a continuous ultra high pressure preservation process suitable for processing foods.

12 Claims, 1 Drawing Sheet

METHOD FOR PRESERVATION UNDER PRESSURE

This application is the national phase of international application PCT/EP97/02711 filed May 15, 1997 which designated the U.S.

The present invention is concerned with a method for preservation, particularly ultra high pressure preservation. The method is used for operation in a continuous mode and is particularly suitable in the food industry.

STATE OF THE ART

Industrially prepared food usually has to be subjected to a preservation treatment in order to prevent spoilage during subsequent storage. Ultra-high pressure (UHP) preservation is a preservation method which only relatively recently has been developed for industrial application, although the lethal effect of ultra-high pressure on micro-organisms has been discovered already in the previous century by B. H. Hite. A review of the state of the art can be found in New Methods of Food Preservation (1995, ed. G. W. Gould). UHP preservation is the subject of many patents: e.g. U.S. Pat. No. 4,873,094, U.S. Pat. No. 5,228,394. NL 102 914 describes conducting a spread-like product through a narrow tube under an initial pressure of 40 atmospheres with a beneficial effect on the consistency of the product. This pressure however, is not high enough to have a significant effect on the viability of micro-organisms in the product.

Substances treated in a homogenizer are exposed also to a very high pressure, but during a very short time (several milliseconds). In such a device the shear forces exerted on the substance during the pressure drop are enormous and often damage the product structure. Moreover the energy needed for passing the product through the homogenizing clearance dissipates quickly in a small volume of the shearing device resulting in a local, unacceptably high temperature rise. Usually this rise is approximately 5° C. per 20 MPa of pressure drop, the rise also depending on the thermal capacity and heat conductivity of the product.

A major disadvantage of known UHP preservation techniques is that UHP preservation is applied only batch-wise. Since 20 most food processing is operated in a continuous mode, an UHP preservation method which could be operated as a continuous process would fulfill a need. Only WO 95/22912 describes UHP equipment with which a semi-continuous process can be carried out. Present equipment for UHP processing is complicated and so expensive that it impedes an economic use and consequently the general employment of UHP preservation.

STATEMENT OF INVENTION

We have found an unexpectedly feasible combination of two seemingly controversial conditions: the one condition being maintenance of a high kinematic pressure in a tube which is relatively narrow and open at the exit end, which kinematic pressure in at least a part of the tube is sufficiently high that a microbiologically contaminated fluid during its flowing through the tube gets decontaminated, the other condition being the realisation of a flow which is high enough to make the process economically feasible.

The invention therefore provides a method for decreasing the viability of micro-organisms and/or the activity of enzymes in a contaminated substance by exerting a high pressure to the substance, characterized in that the substance is conducted in a steady flow through a tube, while the pressure difference between the entrance end and the exit end of the tube is maintained at 100 MPa or more. The present method allows a fully continuous UHP preservation process.

DETAILS OF THE INVENTION

Figure 1:
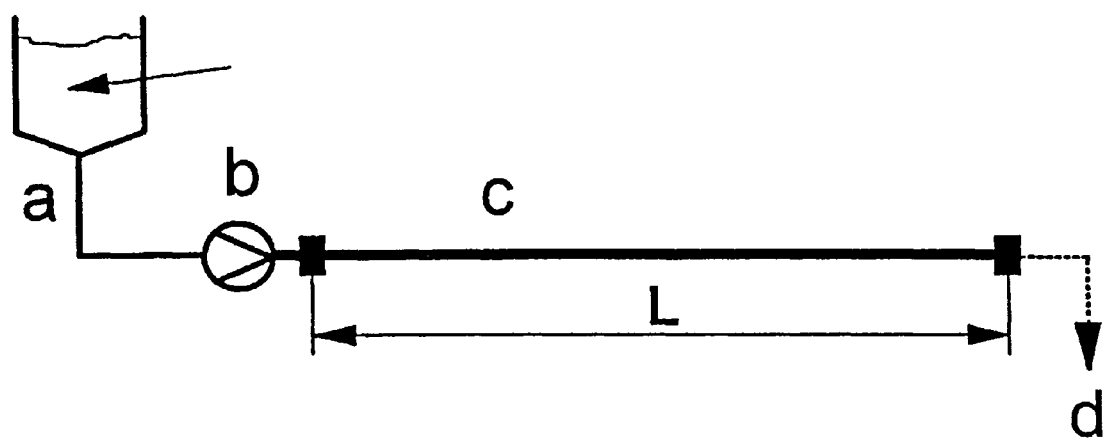
FIG. 1 shows a schematic view of the equipment with which the invention can be carried out. c is a tube with a length L and an inner diameter d. a is a storage container connected to the entrance of the tube via a pressure unit b. At d the open orifice of the tube is situated.

The invention essentially is carried out by feeding the substance from the storage container a to the entrance of the tube via a pressure unit b and passing it through the tube to the exit at the right hand side.

The invention can be applied on all types of fluid substances which need a decontamination treatment, provided they have a consistency which allows a sufficiently quick passage through the necessarily small tubes employed with the invention. Such substances comprise pharmaceutical substances, clinical liquids, and particularly food products such as spreads, mayonnaise, dressings, milk, tea and even heat sensitive products as ice-cream and soft cheese. The invention is particularly suitable for substances which tolerate only gentle treatments. The substance may be a final food product or an ingredient (or a mixture of ingredients) used for the preparation of a 5 food product, including even such nature originating substances as herbs, provided they can be incorporated in a fluid carrier substance which can be pumped through the narrow tube.

In order to maintain a pressure of at least 100 MPa between the entrance and the exit of the tube, a proper balance should be found between on the one side the diameter and length of the tube and on the other side the given viscosity and the desired flow of the product to be treated. The minimum volume V of the tube results from the formula $$V = t * f,$$

where t is the minimum residence time for effective decontamination and f is the desired flow. The residence time can be adjusted without changing the narrow tube dimensions by inserting a chamber at the upstream end of the narrow tube, between the exit of the pressure device and the entrance of the narrow tube. With such chamber the ultra high pressure volume is increased and consequently the residence time of the fluid. Because of its resistance against high pressures, such chamber preferably is a tube too, which diameter is greater than the narrow tube diamter so that pressure drop and flow are not substantially influenced by the presence of the chamber. Preferably such chamber has a diameter which is at least 5 times greater than the narrow tube diameter. The following description of a tube is not applicable to this residence chamber, but rather to the attached narrow tube. Unless it is indicated otherwise, the term tube is used for the narrow tube.

In the context of the present description a tube is considered to be a round vessel with two openings at both ends of the vessel where the length of the vessel is at least ten times the width of the vessel. Generally, the ratio of the length and the average diameter of a tube suitable for the invention is at least 1000, preferably at least 10,000. Generally this means a diameter of only several millimeters and a length of at least several meters. The optimum dimensions can be easily found by some calculation and experimentation. Good results can be obtained with a tube having a length of only 200 m and an internal diameter of 10 mm. It is much surprising that food products which often have a rather viscous consistency can be pressed through such tube at a flow rate sufficient for economic processing. With said open tubes an output per hour of about 50 liter product having an oily viscosity can be realized by exerting a pressure of 1000 MPa. The high flows needed in practice are realized by combining into bundles large numbers of parallel tubes. See also Table I for examples of suitable tube dimensions in relation to given substance viscosity and exerted pressure.

Pressure building in an open tube was believed to be possible only with extremely long tubes. However, an unexpectedly favourable pressure dependent viscosity behaviour is observed.

The pressure within the tube should be at least 100 MPa, but pressures of at least 300 MPa are preferred. Generally higher pressures allow shorter decontamination times.

The ultra high pressures needed for working the invention can be withstood best by tubes with relatively narrow diameters: 10 mm or less is preferred. Special reinforcement is not necessary. The present preservation device does not need the very thick walls of prior art equipment.

TABLE I

| Fluid | P MPa | L m | d m | L/d | Visc. Pa · s | Flow l/h |
|---|---|---|---|---|---|---|
| 1 | 751 | 100 | 0.0010 | 100000 | 0.001 | 50 |
| 2 | 566 | 100 | 0.0010 | 100000 | 0.01 | 50 |
| 3 | 559 | 100 | 0.0015 | 66667 | 0.05 | 50 |
| 4 | 539 | 100 | 0.0018 | 55556 | 0.1 | 50 |
| 5 | 377 | 100 | 0.0035 | 28571 | 1 | 50 |
| 6 | 437 | 100 | 0.0060 | 16667 | 10 | 50 |
| 7 | 566 | 100 | 0.0100 | 10000 | 100 | 50 |
| 8 | 546 | 100 | 0.0012 | 83333 | 0.1 | 10 |
| 9 | 707 | 100 | 0.0020 | 50000 | 0.1 | 100 |
| 10 | 442 | 100 | 0.0040 | 25000 | 0.1 | 1000 |
| 11 | 699 | 1000 | 0.0030 | 333333 | 0.1 | 50 |
| 12 | 566 | 10 | 0.0010 | 10000 | 0.1 | 50 |
| 13 | 354 | 10 | 0.0020 | 5000 | 1 | 50 |

Applicable to fluids having a density of about 1000 kg/m$^3$ and a heat capacity of 4.2 J/g · K
p: pressure drop in Megapascal
d: average diameter of tube in meters
Flow: flow rate in liters per hour
L: length of tube in meters
Visc: viscosity in Pascal seconds The tube may be placed in any position, but preferably a compact form such as a coil is chosen. Tubes having a circular intersection are most advantageous in resisting high pressures, but other forms of intersections are not excluded.

Glass and stainless steel, substances which are compatible with food, are preferred tube materials.

For the pressure device or unit a choice can be made from the devices found on the market which are meant for pumping fluids under ultra high pressures.

In order that the exerted pressure has a sufficient effect on the micro-organisms, the residence time of the fluid in the tube should be at least 1 second. Generally, longer residence times are needed when the pressure is lower than 350 MPa. Preferably the residence time is at least 2 minutes, more preferably at least 5 minutes and still more preferably at least 10 minutes.

It is difficult to give general rules since the flow behaviour of the substance processed under UHP conditions generally can not be predicted. Given a particular substance, some experimentation will easily provide the proper combination of tube dimensions and pressure.

The present device operates with a permanently open orifice at the end of the tube. The effect is a pressure gradient along the whole length of the tube. Consequently the pressure in the tube is higher in upstream parts than in downstream parts of the tube, with the effect that decontamination takes place predominantly in the upstream part of the tube.

High pressure energy is dissipated evenly over the whole length of the tube.

Within the tube the shear forces are relatively small. Moreover both the relatively large external surface of the tube in relation to the volume of the tube and the relatively thin wall of the tube allow an easy control of the temperature of the tube's content if necessary with the help of additional cooling. The temperature rise of the processed substance during tube passage can be confined to less than 10° C., preferably less than 5° C. This fits into modern concepts to avoid as much as possible unnecessary heating of industrially prepared food.

Operating the process at a temperature different from ambient temperature may be advantageous. When the temperature is lowered, the viscosity will increase which makes it possible to maintain the pressure at the desired level even when the fluid to be treated is not sufficiently viscous at ambient temperature.

A temperature increase will cause a lowered viscosity and an advantageous increase of the flow will result. Such increase will meet the obvious limitation that the substance to be treated needs a minimum residence time in the tube.

The present invention gives a method which allows the decontamination of food products where the use of preserving ingredients, a low pH or the use of heating is undesirable.

Nevertheless the present UHP method may be used in combination with one or more other preservation methods. When combining methods, often much less severe over-all conditions will suffice for attaining the required decontamination degree.

A particularly effective combination is the application of lethal pulsating electrical or magnetic fields to the substance when it passes through the high pressure tube.

The process of the invention inactivates vegetative cells. For the inactivation of microbial spores generally a higher pressure and/or a longer exposure time should be applied. Affected micro-organisms include bacteria as well as moulds and yeasts, but also viruses. Although full sterilization of the product in principle is possible, often a lesser degree of decontamination suffices, so that less severe process conditions can be applied.

UHP preservation has the additional advantage that also enzymes are fully or partially deactivated.

In the context of this specification with a substantial decrease in viability is meant a reduction in the viable microorganisms count with a factor 1000 or higher. This is often expressed as logcycle reduction (log (N0/Nt)) which should be 3 or higher. Nt is the count after the process and N0 before the process.

The present method distinguishes itself from prior art methods by its surprising simplicity which not only contributes to economy but also to process reliability.

The invention is further illustrated by the following example:

EXAMPLE 1

In 1000 ml of glycerol 1000 cells per ml of the yeast *Saccharomyces cerevisiae* have been dispersed. The dispersion in which a natural contamination condition was emulated was conducted through a tube with a length of 25 m and a diameter of 1 mm with a pressure of 300 MPa at the entrance of the tube. The residence time in the tube was 60 seconds and the temperature was ambient temperature, 21° C. The substance collected at the end of the tube was assayed on contamination, but no detectable amount of yeast cells could be established.

We claim:

1. In a method for decreasing the viability of microorganisms and/or the activity of enzymes in a contaminated substance by applying a high pressure to the substance, the improvement wherein the substance is conducted in a steady flow through a tube, while the pressure difference between the entrance end and the exit end of the tube is maintained at 100 Mpa or more.

2. Method according to claim 1 wherein the residence time of the substance in the tube is at least 1 second.

3. Method according to claim 1 or claim 2 wherein the substance is a food product or an ingredient for a food product.

4. Method according to claim 1 or claim 2 wherein the ratio of the length and the diameter of the tube is at least 1000.

5. Method according to claim 1 or claim 2 wherein the tube contains at its upstream end a chamber of which the diameter is at least 5 times greater than the remainder of the tube.

6. Method according to claim 1 or claim 2 wherein the temperature rise of the substance during tube passage is less than 10° C.

7. Method according to claim 1 wherein the pressure difference between the entrance end and the exit end of the tube is maintained at 300 Mpa or more.

8. Method according to claim 2 wherein the residence time is at least 2 minutes.

9. Method according to claim 8 wherein the residence time is at least 10 minutes.

10. Method according to claim 4 wherein said ratio is at least 10,000.

11. Method according to claim 5 wherein the chamber is in the form of a tube.

12. Method according to claim 6 wherein the temperature rise is less than 5° C.

* * * * *